United States Patent
Metz

(10) Patent No.: US 10,350,141 B2
(45) Date of Patent: Jul. 16, 2019

(54) SYRINGE HOLDING ASSEMBLY

(71) Applicant: William Metz, Fairbury, IL (US)

(72) Inventor: William Metz, Fairbury, IL (US)

(*) Notice: Subject to any disclaimer, the term of this patent is extended or adjusted under 35 U.S.C. 154(b) by 72 days.

(21) Appl. No.: 15/792,243

(22) Filed: Oct. 24, 2017

(65) Prior Publication Data
US 2019/0117516 A1  Apr. 25, 2019

(51) Int. Cl.
*A61M 5/178* (2006.01)
*A61J 1/20* (2006.01)
*B65B 3/00* (2006.01)
*A61J 1/16* (2006.01)

(52) U.S. Cl.
CPC .............. *A61J 1/2096* (2013.01); *A61J 1/16* (2013.01); *A61J 1/2048* (2015.05); *A61M 5/1782* (2013.01); *B65B 3/003* (2013.01)

(58) Field of Classification Search
CPC ...... B65B 3/003; A61J 1/2096; A61M 5/1782
See application file for complete search history.

(56) References Cited

U.S. PATENT DOCUMENTS

| | | | |
|---|---|---|---|
| 3,833,030 A * | 9/1974 | Waldbauer, Jr. | A61M 5/1782 141/26 |
| 3,853,158 A * | 12/1974 | Whitty | A61J 1/2096 141/233 |
| 4,475,915 A | 10/1984 | Sloane | |
| 4,489,766 A * | 12/1984 | Montada | A61M 5/1782 141/27 |
| 5,468,233 A * | 11/1995 | Schraga | A61M 5/1782 141/27 |
| 5,554,128 A | 9/1996 | Hedges | |
| 5,873,859 A | 2/1999 | Muntz | |
| 5,894,870 A * | 4/1999 | Maxwell | A61J 1/2096 141/25 |
| 6,006,798 A | 12/1999 | Lindquist | |
| 6,364,866 B1 * | 4/2002 | Furr | A61M 5/1782 141/330 |
| D625,805 S | 10/2010 | Hereford | |
| 8,360,114 B2 | 1/2013 | Clark | |
| 9,132,927 B1 | 9/2015 | Larson | |

FOREIGN PATENT DOCUMENTS

WO  WO2011072226  6/2011

* cited by examiner

*Primary Examiner* — Timothy L Maust
*Assistant Examiner* — Timothy P. Kelly

(57) ABSTRACT

A syringe holding assembly for filling a syringe with medication includes a block that has a first well therein to insertably receive a medication bottle. The block has a second well therein to insertably receive a syringe. The first well is aligned with the second well to align the syringe with the medication bottle. In this way a user with limited hand dexterity is assisted to fill the syringe with medication. An adapter is provided to receive a vial. The adapter is removably positioned in the first well thereby facilitating the vial to be aligned with the syringe.

8 Claims, 3 Drawing Sheets

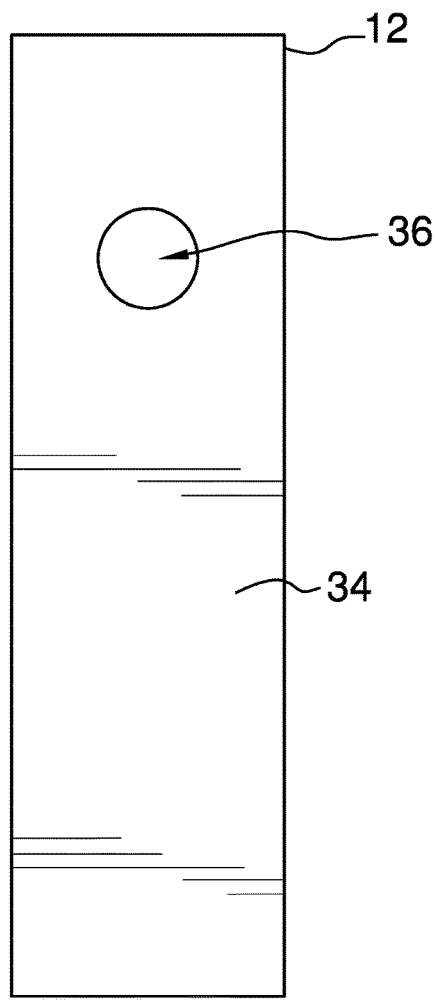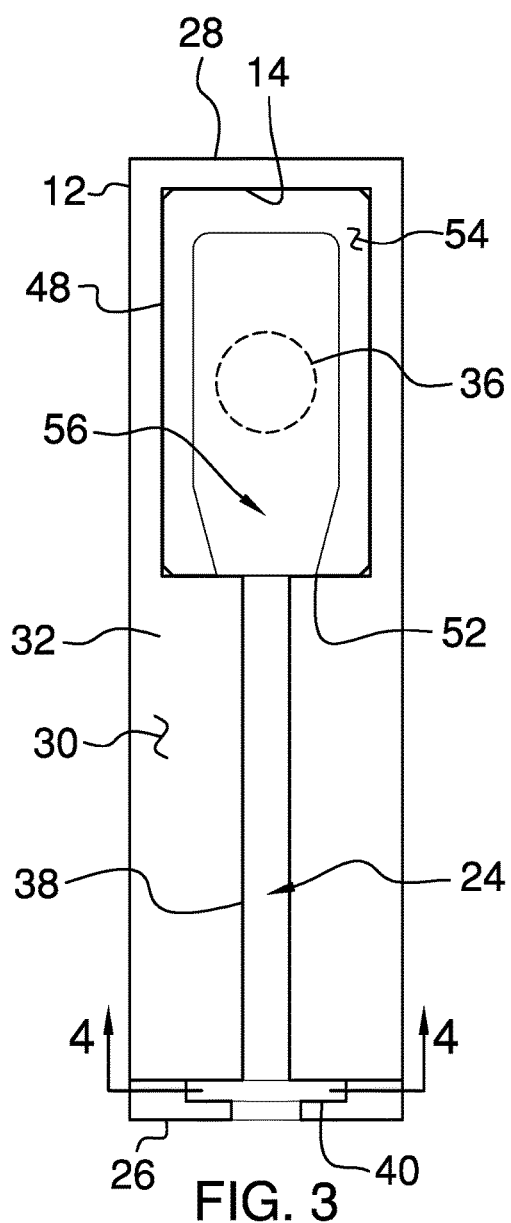
FIG. 2
FIG. 3

SYRINGE HOLDING ASSEMBLY

CROSS-REFERENCE TO RELATED APPLICATIONS

Not Applicable

STATEMENT REGARDING FEDERALLY SPONSORED RESEARCH OR DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC OR AS A TEXT FILE VIA THE OFFICE ELECTRONIC FILING SYSTEM

Not Applicable

STATEMENT REGARDING PRIOR DISCLOSURES BY THE INVENTOR OR JOINT INVENTOR

Not Applicable

BACKGROUND OF THE INVENTION (1) Field of the Invention (2) Description of Related Art Including Information Disclosed Under 37 CFR 1.97 and 1.98

The disclosure and prior art relates to holding devices and more particularly pertains to a new holding device for filling a syringe with medication.

BRIEF SUMMARY OF THE INVENTION

An embodiment of the disclosure meets the needs presented above by generally comprising a block that has a first well therein to insertably receive a medication bottle. The block has a second well therein to insertably receive a syringe. The first well is aligned with the second well to align the syringe with the medication bottle. In this way a user with limited hand dexterity is assisted to fill the syringe with medication. An adapter is provided to receive a vial. The adapter is removably positioned in the first well thereby facilitating the vial to be aligned with the syringe.

There has thus been outlined, rather broadly, the more important features of the disclosure in order that the detailed description thereof that follows may be better understood, and in order that the present contribution to the art may be better appreciated. There are additional features of the disclosure that will be described hereinafter and which will form the subject matter of the claims appended hereto.

The objects of the disclosure, along with the various features of novelty which characterize the disclosure, are pointed out with particularity in the claims annexed to and forming a part of this disclosure.

BRIEF DESCRIPTION OF SEVERAL VIEWS OF THE DRAWING(S)

The disclosure will be better understood and objects other than those set forth above will become apparent when consideration is given to the following detailed description thereof. Such description makes reference to the annexed drawings wherein:

FIG. 2 is a bottom view of an embodiment of the disclosure.

FIG. 3 is a top phantom view of an embodiment of the disclosure.

DETAILED DESCRIPTION OF THE INVENTION

Figure 1:
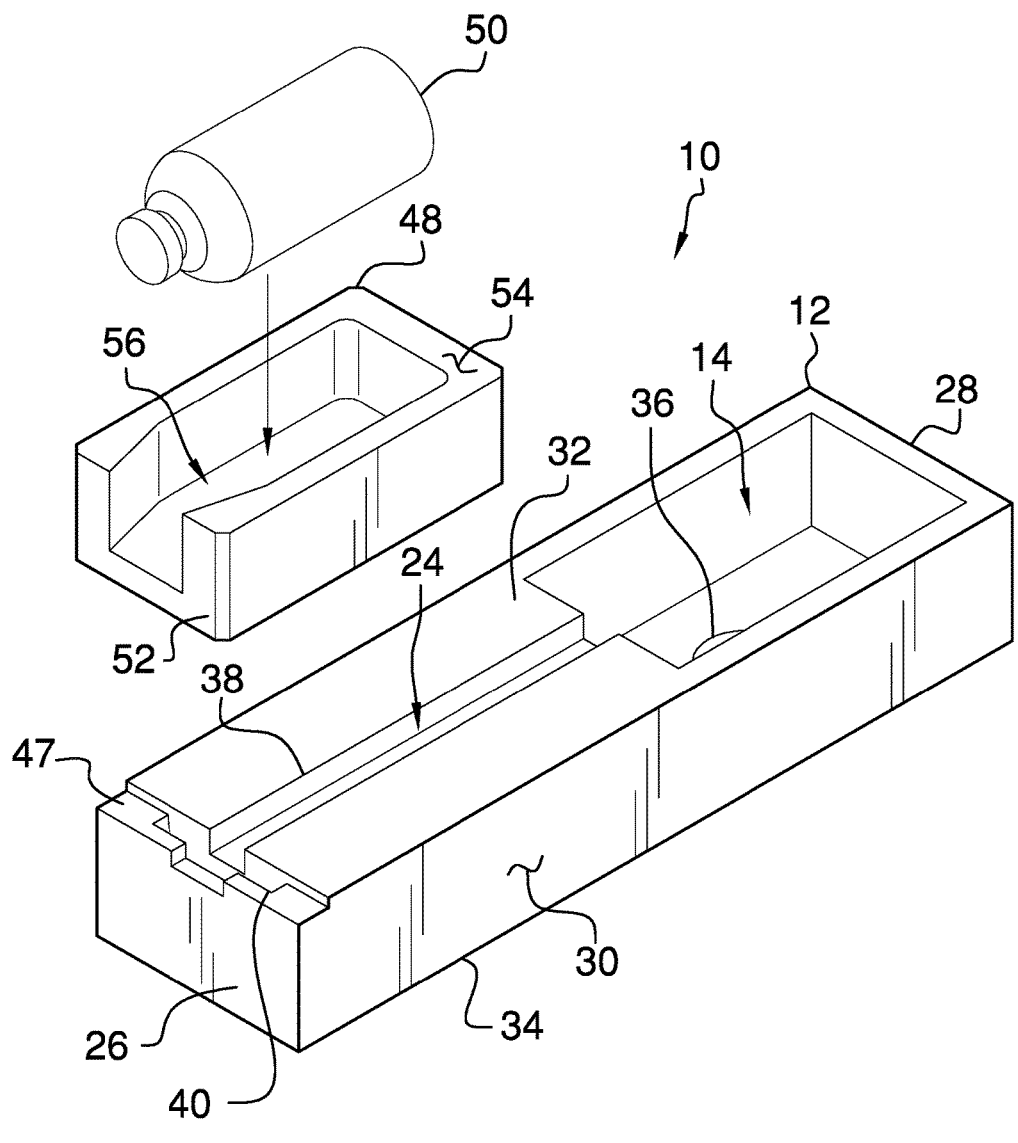
FIG. 1 is a perspective view of a syringe holding assembly according to an embodiment of the disclosure.
Figure 4:
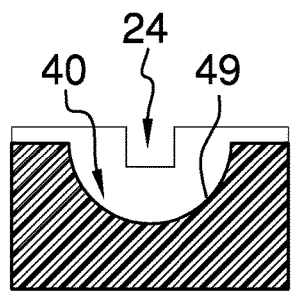
FIG. 4 is a cross sectional view taken along line 4-4 of FIG. 3 of an embodiment of the disclosure.
Figure 5:
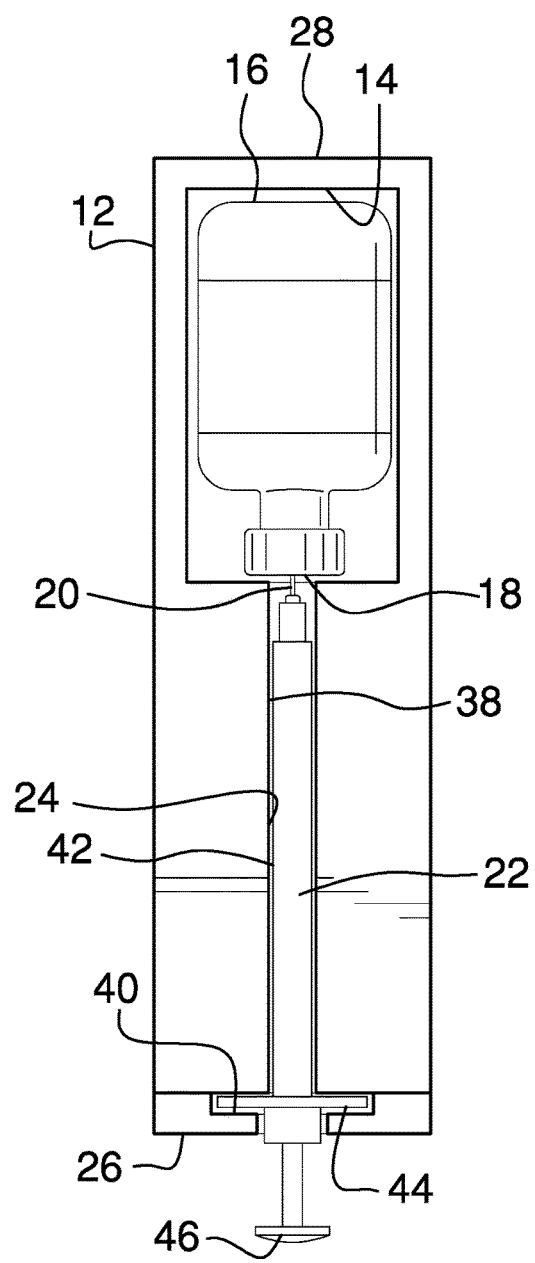
FIG. 5 is a perspective in-use view of an embodiment of the disclosure.

With reference now to the drawings, and in particular to FIGS. 1 through 5 thereof, a new holding device embodying the principles and concepts of an embodiment of the disclosure and generally designated by the reference numeral 10 will be described.

As best illustrated in FIGS. 1 through 5, the syringe holding assembly 10 generally comprises a block 12 that is gripped. The block 12 has a first well 14 therein to insertably receive a medication bottle 16. The medication bottle 16 has a rubber stopper 18 for receiving a needle 20 on a syringe 22. Additionally, the medication bottle 16 contains a liquid medication. The block 12 has a second well 24 therein to insertably receive a syringe 22. The first well 14 is aligned with the second well 24 to align the syringe 22 with the medication bottle 16. In this way a user with limited hand dexterity is assisted to fill the syringe 22 with medication.

The block 12 has a first end 26, a second end 28 and an outer surface 30 extending therebetween. The outer surface 30 has a top side 32 and bottom side 34 and the first well 14 extends through the top side 32 toward the bottom side 34. The first well 14—is position closer to the second end 28 then the first end 26. The bottom side 34 has an aperture 36 extending into the first well 14 to receive a finger for pushing the medication bottle 16 out of the first well 14.

The second well 24 extends through the top side 32 toward the bottom side 34 and the second well 24 has a first portion 38 that is oriented perpendicular to a second portion 40. The first portion 38 extends through the first end 26 and intersects the first well 14. Moreover, the first portion 38 receives a tube 42 of the syringe 22 when the syringe 22 is placed in the block 12. The second portion 40 is spaced from the first end 26 and is oriented collinear with the first end 26.

The second portion 40 receives wings 44 of the syringe 22 having a plunger 46 of the syringe 22 extending outwardly from the first end 26. In this way the syringe 22 is aligned with the medication bottle 16 and the syringe 22 is inhibited from moving when the plunger 46 is manipulated to draw the liquid mediation into the syringe 22. The top side 32 has a recess 47 and the recess 47 is coextensive with the first end 26 of the block 12. Additionally, the second portion 40 of the second well 24 is positioned in the recess 47. The second portion 40 has a lower bounding surface 49 and the lower bounding surface 49 is concavely arcuate to accommodate a disk in lieu of the wings 44 on the syringe 22.

An adapter 48 is provided and the adapter 48 selectively receives a vial 50. The vial 50 may be contains a liquid medication and the vial 50 may have a fluid capacity that is smaller than a fluid capacity of the medication bottle 16. The adapter 48 is removably positioned in the first well 14 thereby facilitating the vial 50 to be aligned with the syringe 22. The adapter 48 has a primary end 52 and an upper surface 54. The upper surface 54 has a third well 56 extending downwardly therein to insertably receive the vial 50. The third well 56 extends through the primary end 52 and the primary end 52 is aligned with first portion 38 of the second well 24 in the block 12. In this way the adapter 48 facilitates the syringe 22 to draw medication from the vial 50.

In use, the medication bottle 16 is placed in the first well 14 such that the rubber stopper 18 in the medication bottle 16 is aligned with the first portion 38 of the second well 24. The syringe 22 is manipulated to simultaneously insert the needle 20 on the syringe 22 through the rubber stopper 18 and to position the syringe 22 in the second well 24. Thus, each of the medication bottle 16 and the syringe 22 are retained in the block 12 to enhance manipulation for a user with comprised hand dexterity. The block 12 is gripped and the plunger 46 on the syringe 22 is urged outwardly to draw a selected amount of the medication into the syringe 22. The vial 50 is positioned in the adapter 48 and the adapter 48 is positioned in the first well 14 to facilitate the medication to be drawn outwardly from the vial 50.

With respect to the above description then, it is to be realized that the optimum dimensional relationships for the parts of an embodiment enabled by the disclosure, to include variations in size, materials, shape, form, function and manner of operation, assembly and use, are deemed readily apparent and obvious to one skilled in the art, and all equivalent relationships to those illustrated in the drawings and described in the specification are intended to be encompassed by an embodiment of the disclosure.

Therefore, the foregoing is considered as illustrative only of the principles of the disclosure. Further, since numerous modifications and changes will readily occur to those skilled in the art, it is not desired to limit the disclosure to the exact construction and operation shown and described, and accordingly, all suitable modifications and equivalents may be resorted to, falling within the scope of the disclosure. In this patent document, the word "comprising" is used in its non-limiting sense to mean that items following the word are included, but items not specifically mentioned are not excluded. A reference to an element by the indefinite article "a" does not exclude the possibility that more than one of the element is present, unless the context clearly requires that there be only one of the elements.

I claim:

1. A syringe holding assembly being configured to align a syringe with a medication bottle thereby facilitating the syringe to be filled with medication, said assembly comprising:

a block being configured to be manipulated, said block having a first well therein wherein said first well is configured to insertably receive the medication bottle, said block having a second well therein wherein said second well is configured to insertably receive the syringe, said first well being aligned with said second well wherein each of said first well and said second well are configured to align the syringe with the medication bottle thereby facilitating a user with limited hand dexterity to fill the syringe with medication; and an adapter being configured to receive a vial, said adapter being removably positioned in said first well thereby facilitating the vial to be aligned with the syringe.

2. The assembly according to claim 1, wherein said block has a first end, a second end and an outer surface extending therebetween, said outer surface having a top side and bottom side, said first well extending through said top side toward said bottom side, said first well-being position closer to said second end then said first end.

3. The assembly according to claim 2, wherein said bottom side has an aperture extending into said first well wherein said aperture is configured to receive a finger for pushing the medication bottle out of said first well.

4. The assembly according to claim 3, wherein said second well extends through said top side toward said bottom side, said second well having a first portion being oriented perpendicular to a second portion, said first portion extending through said first end and intersecting said first well wherein said first portion is configured to receive a tube of the syringe.

5. The assembly according to claim 4, wherein said second portion is spaced from said first end and being oriented collinear with said first end wherein said second portion is configured to receive wings of the syringe having a plunger of the syringe extending outwardly from said first end.

6. The assembly according to claim 4, wherein said adapter has a primary end and an upper surface, said upper surface having a third well extending downwardly therein wherein said third well is configured to insertably receive the vial, said third well extending through said primary end.

7. The assembly according to claim 6, wherein said primary end is aligned with first portion of said second well in said block wherein said adapter is configured to facilitate the syringe to draw medication from the vial.

8. A syringe holding assembly being configured to align a syringe with a medication bottle thereby facilitating the syringe to be filled with medication, said assembly comprising:

a block being configured to be manipulated, said block having a first well therein wherein said first well is configured to insertably receive the medication bottle, said block having a second well therein wherein said second well is configured to insertably receive the syringe, said first well being aligned with said second well wherein each of said first well and said second well are configured to align the syringe with the medication bottle thereby facilitating a user with limited hand dexterity to fill the syringe with medication, said block having a first end, a second end and an outer surface extending therebetween, said outer surface having a top side and bottom side, said first well extending through said top side toward said bottom side, said first well-being position closer to said second end then said first end, said bottom side having an aperture extending into said first well wherein said aperture is configured to receive a finger for pushing the medication bottle out of said first well, said second well extending through said top side toward said bottom side, said second well having a first portion being oriented perpendicular to a second portion, said first portion extending through said first end and intersecting said first well wherein said first portion is configured to receive a tube of the syringe, said second portion being spaced from said first end and being oriented collinear with said first end wherein said second portion is configured to receive wings of the syringe having a plunger of the syringe extending outwardly from said first end; and an adapter being configured to receive a vial, said adapter being removably positioned in said first well thereby facilitating the vial to be aligned with the syringe, said adapter having a primary end and an upper surface, said upper surface having a third well extending downwardly therein wherein said third well is configured to insertably receive the vial, said third well extending through said primary end, said primary end being aligned with first portion of said second well in said block wherein said adapter is configured to facilitate the syringe to draw medication from the vial.

\* \* \* \* \*